(12) United States Patent
Natesan et al.

(10) Patent No.: US 11,865,274 B2
(45) Date of Patent: Jan. 9, 2024

(54) CATHETER SYSTEM FOR PEDIATRIC TREATMENT

(71) Applicant: Becton, Dickinson and Company, Franklin Lakes, NJ (US)

(72) Inventors: Mohankumar Natesan, Bukit Batok (SG); Ong Xue Guang John, Ghim Moh (SG)

(73) Assignee: Becton, Dickinson and Company, Franklin Lakes, NJ (US)

( * ) Notice: Subject to any disclaimer, the term of this patent is extended or adjusted under 35 U.S.C. 154(b) by 0 days.

(21) Appl. No.: 16/989,243

(22) Filed: Aug. 10, 2020

(65) Prior Publication Data

US 2021/0060307 A1   Mar. 4, 2021

Related U.S. Application Data

(60) Provisional application No. 62/892,738, filed on Aug. 28, 2019.

(51) Int. Cl.
*A61M 25/06* (2006.01)
*A61M 25/02* (2006.01)

(52) U.S. Cl.
CPC .... *A61M 25/0612* (2013.01); *A61M 25/0606* (2013.01); *A61M 25/0637* (2013.01);
(Continued)

(58) Field of Classification Search
CPC ............ A61M 25/067; A61M 25/0612; A61M 25/0606; A61M 2025/0253; A61M 2025/0266; A61M 2240/00; A61M 25/0097; A61M 25/0637; A61M 25/02; A61M 2025/0042; A61M 5/158; A61M 2005/1586; A61M 2005/1585; A61B 5/15074

See application file for complete search history.

(56) References Cited

U.S. PATENT DOCUMENTS 3,589,361 A * 6/1971 Loper ............... A61M 25/0631
                                                    604/177
4,324,236 A * 4/1982 Gordon ............. A61M 25/0637
                                                    128/DIG. 26

(Continued)

FOREIGN PATENT DOCUMENTS

CN     103706018 A    4/2014
WO       0112253 A1    2/2001

*Primary Examiner* — Katherine H Schwiker
*Assistant Examiner* — Robert F Allen
(74) *Attorney, Agent, or Firm* — Kirton McConkie; Whitney Blair; Kevin Stinger

(57) ABSTRACT

A pediatric catheter system may include a catheter adapter having a distal end, a proximal end, and a lumen extending therebetween. The lumen may include an upper surface and a lower surface with an adhesive coupled to the lower surface. The system may include a plurality of wings that extend outwardly from the catheter adapter. The plurality of wings may be configured to fold upwardly. The system may include a catheter cannula extending distally from the catheter adapter. The system may include a needle hub removably coupled to a proximal end of the catheter adapter and an introducer needle extending through the catheter tube. A proximal end of the introducer needle may be secured within the needle hub.

5 Claims, 5 Drawing Sheets

(52) U.S. Cl.
CPC ............... *A61M 2025/0253* (2013.01); *A61M 2025/0266* (2013.01); *A61M 2240/00* (2013.01)

(56) References Cited

U.S. PATENT DOCUMENTS

| | | | | |
|---|---|---|---|---|
| 4,629,452 | A * | 12/1986 | Wahlberg | A61M 25/0637 604/164.11 |
| 8,827,960 | B2 * | 9/2014 | Haak | D04H 3/011 604/174 |
| 10,737,059 | B2 * | 8/2020 | Bornhoft | A61M 25/0097 |
| 2004/0116856 | A1 * | 6/2004 | Woehr | A61M 25/0625 604/110 |
| 2005/0137528 | A1 * | 6/2005 | Wilkinson | A61M 25/0637 604/110 |
| 2009/0054845 | A1 | 2/2009 | Puhasmagi et al. | |
| 2012/0053523 | A1 * | 3/2012 | Harding | A61M 25/0612 604/164.08 |
| 2013/0085474 | A1 * | 4/2013 | Charles | A61M 39/162 604/218 |
| 2013/0150791 | A1 | 6/2013 | Peterson et al. | |
| 2014/0128814 | A1 * | 5/2014 | Peterson | A61M 25/02 604/179 |
| 2014/0135652 | A1 * | 5/2014 | Wilkinson | A61B 5/15003 600/576 |
| 2017/0120009 | A1 * | 5/2017 | Garrison | A61M 25/0637 |
| 2017/0296782 | A1 * | 10/2017 | Bornhoft | A61M 25/0606 |
| 2018/0318557 | A1 | 11/2018 | Burkholz et al. | |
| 2018/0339135 | A1 * | 11/2018 | Nathan | A61M 5/3202 |

\* cited by examiner

CATHETER SYSTEM FOR PEDIATRIC TREATMENT

RELATED APPLICATIONS

This application claims the benefit of U.S. Provisional Patent Application No. 62/892,738, filed Aug. 28, 2019 and entitled CATHETER SYSTEM FOR IMPROVED PEDIATRIC TREATMENT which is incorporated herein in its entirety.

BACKGROUND

Infusion therapy, a common healthcare procedure, may be facilitated by a vascular access device. Hospitalized, home care, and other patients receive fluids, pharmaceuticals, and blood products via a vascular access device inserted into the vascular system. Blood withdrawal is another common healthcare procedure that may be facilitated by a vascular access device.

A vascular access device may access a peripheral or central vasculature of a patient. A vascular access device may be indwelling for short term (days), moderate term (weeks), or long term (months to years). A vascular access device may be used for continuous infusion therapy or for intermittent therapy.

A common type vascular access device is an over-the-needle peripheral intravenous catheter (PIVC). As its name implies, the "over-the-needle" PIVC may be mounted over an introducer needle having a sharp distal tip. The sharp distal tip may be used to pierce skin and the vasculature of the patient. Insertion of the PIVC into the vasculature may follow the piercing of the vasculature by the needle. The needle and the PIVC are generally inserted at a shallow angle through the skin into the vasculature of the patient with a bevel of the needle facing away from the skin of the patient.

In pediatric patients, including neonates, where veins may be smaller and more difficult to access, in an attempt to position the PIVC in a vein, catheter placement may be more difficult. Thus, in some instances, more vulnerable patients, including children, may receive more needle sticks, which may result in pain and other complications. Traditional vascular access devices have not adequately addressed these issues. Therefore, a catheter system that mitigates difficulties that arise in pediatric care is needed.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates to catheter systems and related devices and methods configured to facilitate catheter insertion. The catheter system may reduce complications that may be associated with insertion of a catheter tube into a vein of a patient. The catheter system may be particularly useful for pediatric patients, including neonates, to improve catheter placement in smaller veins. It may also reduce the risk that these more vulnerable patients experience unnecessary needle sticks.

In some embodiments, the catheter system may include a catheter adapter having a distal end, a proximal end, and a lumen extending therebetween. An outer surface of the lumen may include an upper surface and a lower surface. The lower surface may include an adhesive. The adhesive may be an integrated tape strip that includes a removable backing layer. The system may include a catheter cannula extending distally from the catheter adapter. A needle hub may also be included in the system that may be removably coupled to a proximal end of the catheter adapter and an introducer needle extending through the catheter tube. A proximal end of the introducer needle may be secured within the needle hub.

In some embodiments, the catheter system may include a pediatric catheter system. In such pediatric catheter systems, the catheter tube may be 24 gauge or 26 gauge. A length of the catheter tube may be approximately 14 mm and the catheter cannula may include a peripheral intravenous catheter.

In some embodiments, the catheter adapter may include one or more wings, which may extend outwardly from the catheter adapter. The wings may be configured to fold upwardly. The one or more wings may include a first surface and a second surface where an adhesive may be coupled to the second surface.

In some embodiments, the catheter system may include a housing, which may be removably coupled to the catheter adapter. The housing may fit over the catheter adapter and secure the wings in an upward position. The housing may also include a finger grip, which may extend outwardly from a distal end of the housing. The housing may be removed from over the catheter adapter to extend the plurality of wings.

In some embodiments, the catheter adapter further comprises a push tab that extends upwardly from the upper surface of the catheter adapter. The catheter adapter may include a first push tab and a second push tab that extend upwardly from between the plurality of wings.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which.

It is to be understood that the Figures are for purposes of illustrating the concepts of the present disclosure and may not be drawn to scale. Furthermore, the Figures illustrate exemplary embodiments and do not represent limitations to the scope of the present disclosure.

DESCRIPTION OF EMBODIMENTS

Exemplary embodiments of the present disclosure will be best understood by reference to the Figures, wherein like parts are designated by like numerals throughout. It will be readily understood that the components of the present disclosure, as generally described and illustrated in the Figures herein, could be arranged and designed in a wide variety of different configurations. Thus, the following more detailed description of the embodiments of the apparatus and systems, as represented in the Figures, is not intended to limit the scope of the present disclosure, as claimed in this or any other application claiming priority to this application, but is merely representative of exemplary embodiments of the present disclosure.

Figure 1:
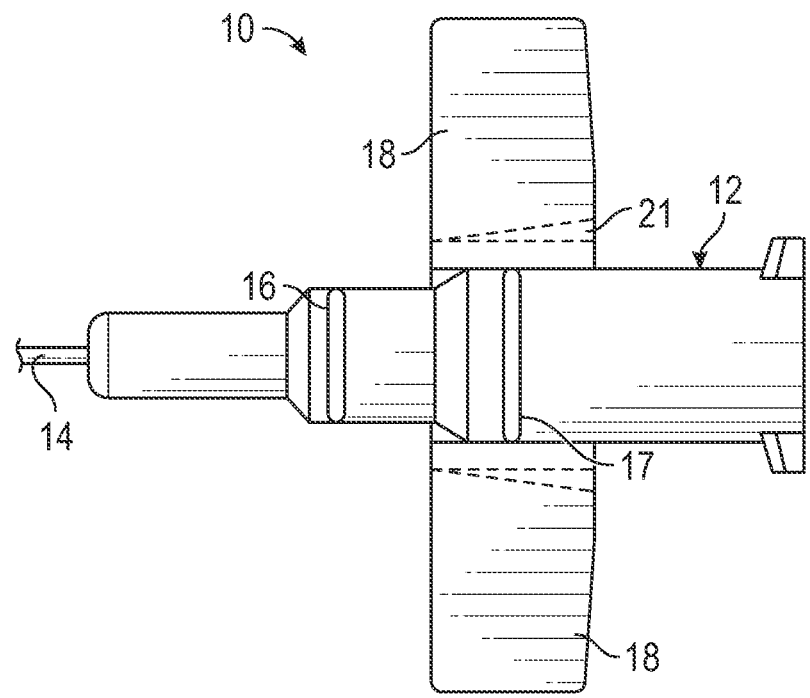
FIG. 1 is a top plan view of one embodiment of a catheter assembly.

Referring now to FIG. 1, an embodiment of a catheter system 10 is illustrated. The catheter system 10 may be similar to the BD Neoflon™ IV Cannula System or another suitable catheter system. For pediatric use, especially neonatal patients with capillary brittleness and where a non-traumatic and delicate needle may be preferred, a smaller gauge cannula and catheter may be preferred for patient comfort during a catheter insertion and/or indwell period.

In some embodiments, the catheter system 10 may include a catheter adapter 12 and a catheter cannula 14. The catheter cannula 14 may extend distally from the catheter adapter 12. In some embodiments, the catheter cannula 14 may include a small gauge catheter sized for a pediatric patient, which may include, for example, a neonatal patient. For example, the catheter cannula 14 may have a gauge size of 24 or smaller. In these and other embodiments, the catheter cannula 14 may include an external diameter approximately equal to 0.7 mm and/or a length approximately equal to 14 mm. In some embodiments, a water flow rate through the catheter cannula 14 may be approximately 20 ml/min. As another example, the catheter cannula 14 may have a gauge size of 26. In these and other embodiments, the catheter cannula 14 may include an external diameter approximately equal to 0.6 mm and/or a length approximately equal to 14 mm. In some embodiments, a water flow rate through the catheter cannula 14 may be approximately 13 ml/min. The appropriate needle gauge and length may be determined by a number of factors, including the target body tissue, injection formulation and/or viscosity, and patient proportions.

In some embodiments, the catheter cannula 14 may be constructed of thermoplastic polyurethane ("TPU") or another suitable material. The catheter cannula 14 may be constructed solely or partially of TPU. The TPU or other suitable material may facilitate a smooth insertion of the catheter cannula 14 into the vein of the patient or may provide less resistance as a user inserts the catheter cannula 14 into the vein than a standard catheter tube. A standard catheter tube may be constructed of polytetrafluoroethylene ("PTFE") or a similar material, which may be difficult to insert into the vein of the patient, providing resistance which may lead to collapse of the standard catheter tube. The catheter cannula 14 constructed of TPU or other suitable material may ease insertion into the vein of the patient and help avoid collapse of the catheter cannula 14 during insertion. Further, the catheter cannula 14 constructed of TPU may reduce a risk of phlebitis and extend an indwelling period of the catheter cannula 14.

In some embodiments, the catheter adapter 12 may include a distal end, a proximal end, and a lumen extending therebetween. In some embodiments, an outer surface of the lumen may include an upper surface and a lower surface. The upper surface of the lumen may include a push tab 16 to withdraw the needle after insertion. In some embodiments, the upper surface of the lumen may include a second push tab 17. In some embodiments, the push tab 16 and/or push tab 17 may enable a clinician to improve the control of the catheter adapter 12 during use.

In some embodiments, the catheter adapter 12 may include one or more wings 18, which may extend outwardly from the catheter adapter 12 to retain the catheter in place. The wings 18 may extend from a lower portion of the catheter adapter 12. The catheter adapter 12 may be constructed of a relatively flexible plastic. In some embodiments, the wings 18 may include a scoring 21 to facilitate the wings 18 folding to an upward and/or downward position.

Figure 2A:
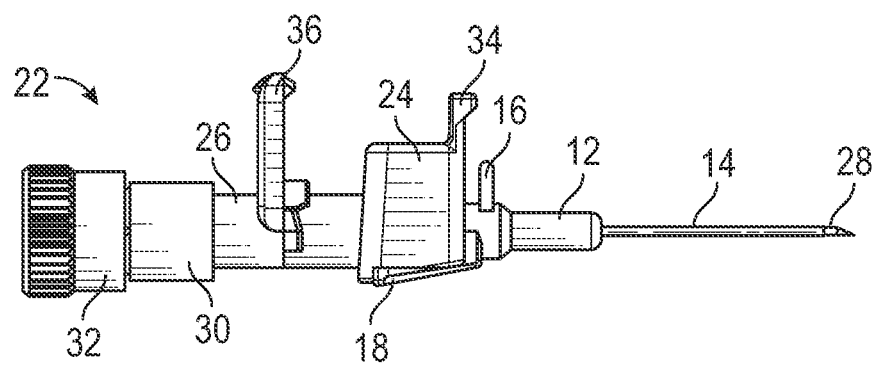
FIG. 2A is a side perspective view of one embodiment of a catheter system.
Figure 2B:
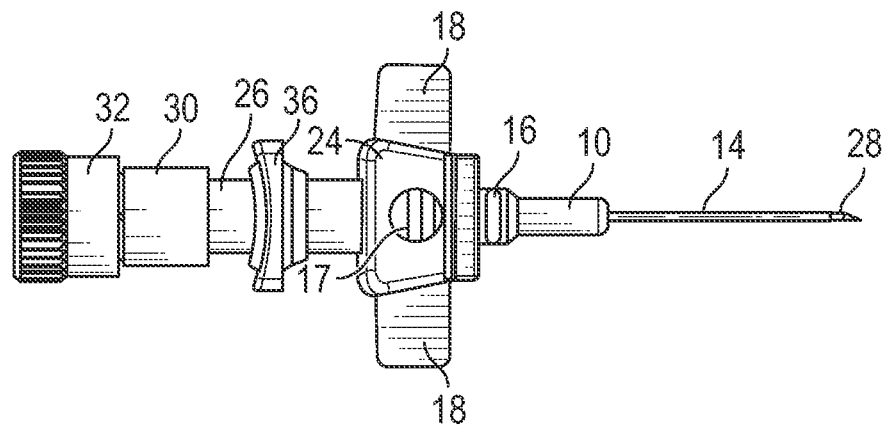
FIG. 2B is a top perspective view of the catheter system of FIG. 2A.

Referring now to FIGS. 2A-2B, a catheter system 22 is illustrated. In some embodiments, the catheter system 22 may include one or more of the following: the catheter adapter 12, the catheter cannula 14, a housing 24, a needle hub 26, a needle 28, a flow control plug 30, and an end cap 32. The housing 24 may be removably coupled to the catheter adapter 12. The housing 24 may be useful for the user, such as a clinician, to grip during insertion of the catheter cannula 14 into the vein of the patient. Also, the housing 24 may provide a larger surface area to grip as compared to the catheter adapter 12 itself. In some embodiments, the housing 24 may further include a finger grip 34 configured to aid in insertion and/or withdrawal of the catheter system 10 from a patient. The housing finger grip 34 may extend outwardly from a distal end of the housing 24. The housing 24 may be generally square to fit over the wings and hold them in an upward position. When the catheter system 22 is in an insertion position prior to inserting the catheter system 22 into the patient, the wings 18 may be disposed in the upward position within the housing 24, as will be explained in further detail.

In some embodiments, a proximal end of the needle 28 may be secured within the needle hub 26. The proximal end of the needle 28 may be press-fit within the needle hub 26. The needle 28 may include an introducer needle having a sharp distal tip to facilitate insertion of the catheter cannula 14 into a vein of the patient. In some embodiments, the needle hub 26 may include a thumb grip 36, which may be configured to aid in removal of the needle hub 26 and needle 28 from the catheter system 10, after the catheter cannula 14 is inserted into the vein of the patient. The needle 28 may be constructed of stainless steel or another suitable material.

In some embodiments, the flow control plug 30 may be configured to vent air, such as, for example, with a semipermeable membrane, porous membrane, and/or micro grooves disposed within the flow control plug 30, but may contain blood. An end cap 32 may be coupled to the proximal end of the flow control plug 30. The end cap 32 may prevent venting of the flow control plug 30 when the end cap 32 is secured to the flow control plug 30. The end cap 32 and/or proximal end of the flow control plug 30 may include a luer adapter, such as a slip or thread male or female luer adapter, or another suitable connector, which may facilitate coupling of the end cap 32 and the flow control plug 30. In some embodiments, an extension tube may be coupled to the luer adapter.

A lumen may extend from a distal end of the catheter adapter 12 to a proximal end of the catheter adapter. A proximal end of the catheter adapter 12 may include a luer adapter, such as a slip or thread male or female luer adapter, or another suitable connector. A distal end of the needle hub 26 may include a connector configured to couple with the connector of the proximal end of the catheter adapter 12. For example, the distal end of the needle hub 26 may include a luer adapter, such as a slip or thread male or female luer adapter, or another suitable connector.

Figure 2C:
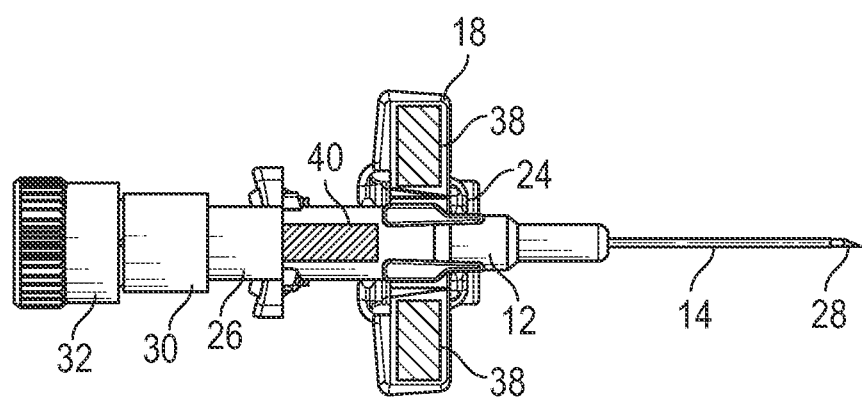
FIG. 2C is a bottom perspective view of the catheter system of FIG. 2A.

Referring now to FIG. 2C, the catheter system 22 of FIGS. 2A-2C is illustrated in a position corresponding to after insertion of the catheter cannula 14 into the vein of the patient but prior to removal of the needle 28. In this position, the wings 18 may be disposed in a downward position for securement to skin of the patient via an adhesive 38. In some embodiments, the wings 18 include a first surface and a second surface. The second surface of the wings 18 may be configured to contact the skin of the patient when the wings are disposed in the downward position. The adhesive 38 may be applied to the second surface so that the wings 18 may be secured to the skin. The adhesive 38 may be an integrated tape strip. In some embodiments, the adhesive 38 may include a backing layer that is removable prior to securement of the wings to the skin of the patient. The catheter adapter 12 may include an upper surface and a lower surface. In some embodiments, the lower surface of the catheter adapter includes an adhesive 40 that secures the catheter adapter 12 to the skin of the patient. The adhesive 38, 40 may avoid catheter dislodgement in case there is an unexpected movement by the patient.

Figure 2D:
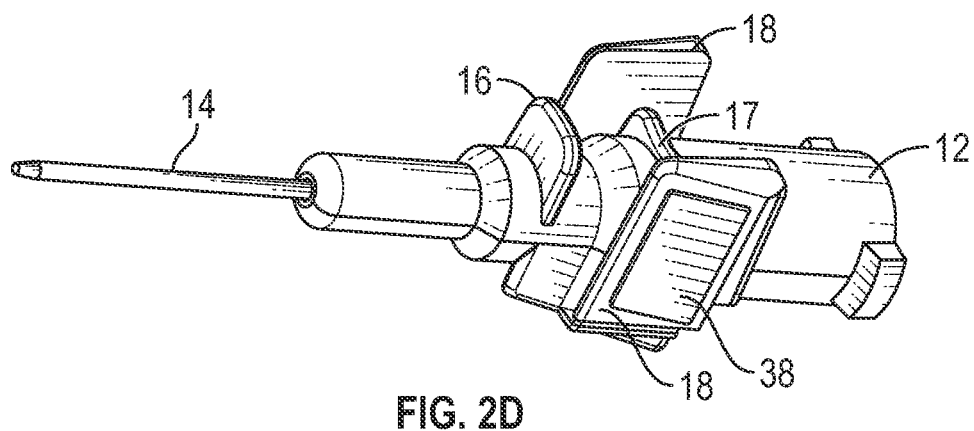
FIG. 2D is a side perspective view of the catheter system of FIG. 2A.
Figure 2E:
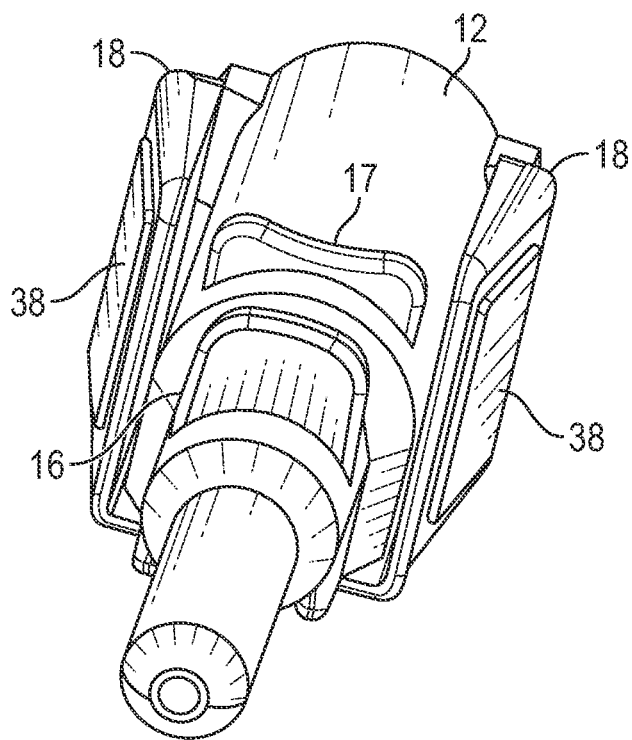
FIG. 2E is a front perspective view of the catheter system of FIG. 2A.
Figure 2F:
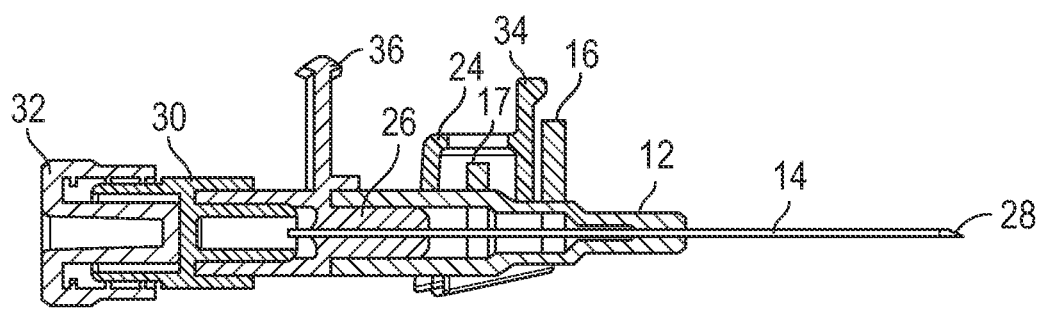
FIG. 2F is a cross-sectional view of the catheter system of FIG. 2A.

Referring now to FIGS. 2D-2F, in some embodiments, the upper surface of the catheter adapter 12 may include a push tab 16. The push tab 16 may extend upwardly from the upper surface of the catheter adapter 12. The push tab 16 may be distal to the housing 24 to be more accessible to the user. In some embodiments, the push tab 16 may be a first push tab and the catheter adapter 12 may include a second push tab 17 that extends upwardly from between the plurality of wings. The second push tab 17 may not extend as far as the first push tab 16 so that the second push tab 17 fits underneath the housing 24. The first push tab 16 and/or the second push tab 17 may enable the clinician to control the catheter adapter 12 during removal and/or insertion.

Before insertion of the needle 28 and the catheter cannula 14 into the patient, the housing 24 may be removed. Upon removal, the first push tab 16 and/or the second push tab 17 may enable a clinician to withdraw the needle 28 after insertion into the vein of the patient. The first push tab 16 and/or the second push tab 17 may provide a surface or grip that a clinician uses to separate the needle hub 26 from the catheter adapter 12. Further, the first push tab 16 and/or the second push tab 17 may enable the user to separate the needle hub 26 from the catheter adapter 12 with one hand.

Figure 3:
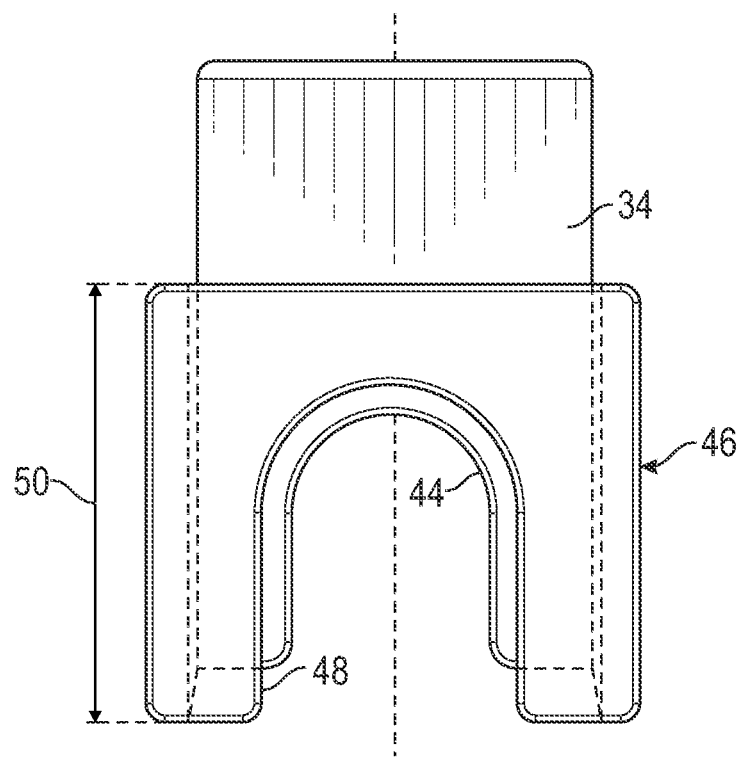
FIG. 3 is a front plan view of an example housing of the catheter system of FIG. 2A.

Referring now to FIG. 3, in some embodiments, the housing 24 may include a distal wall 42, which may include a first arched gate 44, and proximal wall 46 (illustrated, for example, in FIG. 4), which may include a second arched gate 48. The first arched gate 44 and the second arched gate 48 may each include a width that is slightly larger than a diameter of the catheter adapter 12, such that the housing 24 may be pushed with a sliding fit over the catheter adapter 12. The gates 44, 48 may embrace the catheter adapter 12 ahead of and/or behind the wings 18. Also, a height 50 of the housing 24 may be at least a same dimension as a length of wings 18.

Figure 4:
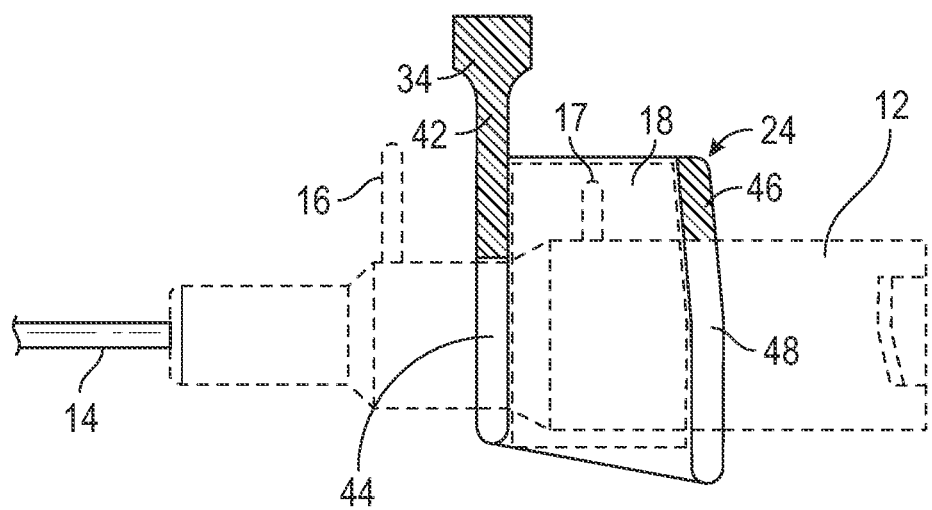
FIG. 4 is a cross-sectional view of one embodiment of a catheter system illustrating the housing mounted on an example catheter adapter.

Referring now to FIG. 4, in some embodiments, the wings 18 may be folded upwardly, and then the housing 24, having an opening in at least a bottom portion, may be pushed with the sliding fit over the catheter adapter 12, securing the wings 18 within the housing 24. After or prior to the normal manipulations, i.e. vein puncture, positive insertion of the catheter cannula 14 into the vein, and separation of the needle hub 26 from the catheter adapter 12, have been carried out by means of the housing finger grip 34 and/or the thumb grip 36, the housing 24 may be removed from the catheter adapter 12, and the wings 18 may be unfolded and then fixed to skin of the patient.

Figure 5:
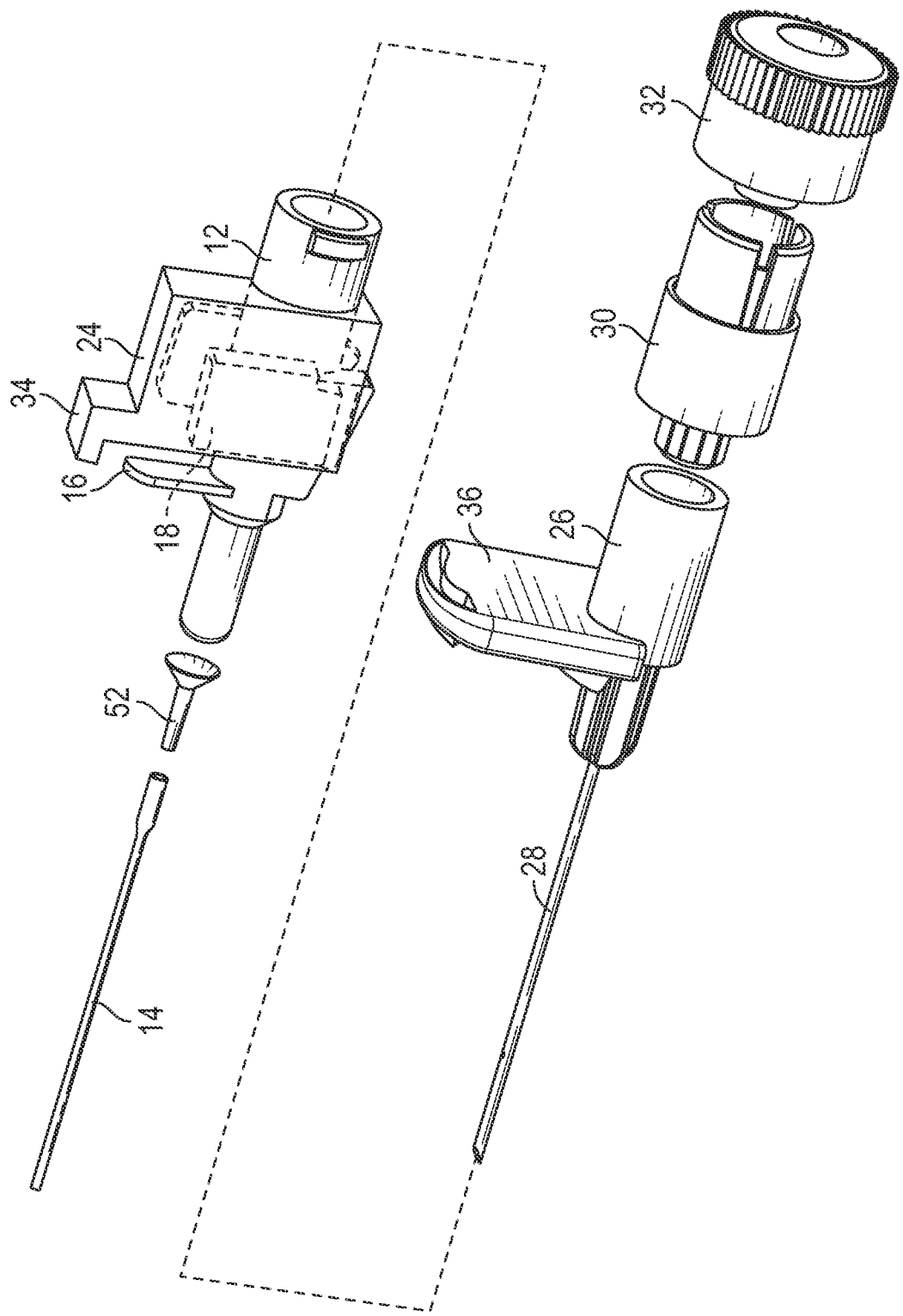
FIG. 5 is an exploded view of the catheter system of FIG. 2A.

Referring now to FIG. 5, a wedge 52 is illustrated, according to some embodiments. The wedge 52 may secure the catheter cannula 14 within the catheter adapter 12. The wedge 52 may be constructed of metal, plastic, or another suitable material.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment. It is to be understood that any of the embodiments of the present disclosure, or any portion(s) of any of the embodiments of the present disclosure, may be combined together in any number of different ways.

Similarly, it should be appreciated that in the above description of embodiments, various features are sometimes grouped together in a single embodiment, Figure, or description thereof for the purpose of streamlining the disclosure. This disclosure format, however, is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Description Of Embodiments are hereby expressly incorporated into this Description Of Embodiments, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

Standard medical directions, planes of reference, and descriptive terminology are employed in this specification. For example, anterior means toward the front of the body. Posterior means toward the back of the body. Superior means toward the head. Inferior means toward the feet. Medial means toward the midline of the body. Lateral means away from the midline of the body. Axial means toward a central axis of the body. Abaxial means away from a central axis of the body. Ipsilateral means on the same side of the body. Contralateral means on the opposite side of the body. A sagittal plane divides a body into right and left portions. A midsagittal plane divides the body into bilaterally symmetric right and left halves. A coronal plane divides a body into anterior and posterior portions. A transverse plane divides a body into superior and inferior portions. These descriptive terms may be applied to an animate or inanimate body.

The phrases "connected to," "coupled to," "engaged with," and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

As defined herein, "substantially equal to" means "equal to," or within about a + or −10% relative variance from one another.

The word "exemplary" is used herein to mean "serving as an example, instance, or illustration." Any embodiment described herein as "exemplary" is not necessarily to be construed as preferred or advantageous over other embodiments. While the various aspects of the embodiments are presented in the Figures, the Figures are not necessarily drawn to scale unless specifically indicated.

While specific embodiments and applications of the present disclosure have been illustrated and described, it is to be understood that the scope of the appended claims is not limited to the precise configuration and components disclosed herein. Various modifications, changes, and variations which will be apparent to those skilled in the art may be made in the arrangement, operation, and details of the apparatus and systems disclosed herein.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present disclosure have been described in detail, it should be understood that the various changes, substitutions, and alterations could be made hereto without departing from the spirit and scope of the present disclosure.

The invention claimed is:

1. A pediatric catheter system, comprising:
a catheter adapter having a distal end, a proximal end, and a lumen extending therebetween, wherein an outer surface of the lumen comprises an upper surface and a lower surface, wherein the catheter adapter further comprises a first push tab distal to a plurality of wings and a second push tab extending upwardly from between the plurality of wings;
the plurality of wings extend outwardly from the catheter adapter, wherein the plurality of wings are configured to fold upwardly;
a housing, wherein the housing is disposed over the catheter adapter and secures the plurality of wings in an upward position, wherein the first push tab is distal to the housing, wherein the second push tab is disposed within the housing and fits underneath the housing, wherein the housing comprises a finger grip;
a catheter cannula extending distally from the catheter adapter;
a needle hub removably coupled to the proximal end of the catheter adapter, wherein the needle hub comprises a thumb grip, wherein a height of the thumb grip is greater than a height of the first push tab, a height of the second push tab, and a height of the finger grip, wherein when the plurality of wings are in the upward position, a height of the plurality of wings is greater than the height of the second push tab; and
an introducer needle extending through the catheter cannula, wherein a proximal end of the introducer needle is secured within the needle hub.

2. The pediatric catheter system of claim 1, wherein a length of the catheter cannula is approximately 14 mm.

3. The pediatric catheter system of claim 1, wherein an adhesive is coupled to the lower surface of the outer surface of the lumen, wherein the adhesive comprises an integrated tape strip having a removable backing layer.

4. The pediatric catheter system of claim 1, wherein the plurality of wings comprise an upper surface and a lower surface, wherein the lower surface of the plurality of wings comprises an adhesive.

5. The pediatric catheter system of claim 1, wherein the housing is configured to be removed to extend the plurality of wings.

* * * * *